US00PP29427P3

(12) United States Plant Patent
Koppe

(10) Patent No.: US PP29,427 P3
(45) Date of Patent: Jun. 26, 2018

(54) ***BEGONIA* PLANT NAMED 'KRHARPI01'**

(50) Latin Name: *Begonia×hiemalis*
Varietal Denomination: KRHARPI01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 3 days.

(21) Appl. No.: 15/330,765

(22) Filed: Nov. 5, 2016

(65) Prior Publication Data

US 2018/0132411 P1 May 10, 2018

(51) Int. Cl.
*A01H 5/02* (2018.01)

(52) U.S. Cl.
USPC ..... Plt./348

(58) Field of Classification Search
USPC ..... Plt./343, 344, 348
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'KRHARPI01' characterized by its upright to somewhat outwardly spreading and mounded plant habit; moderately vigorous growth habit; freely flowering habit; double flowers that are pinkish red in color and held above the foliar plane; and excellent postproduction longevity.

2 Drawing Sheets

Botanical designation: *Begonia×hiemalis*.
Cultivar denomination: 'KRHARPI01'.

BACKGROUND OF THE INVENTION

The present invention relates to a new and distinct cultivar of *Begonia* plant, botanically known as *Begonia×hiemalis*, commercially referred to as an Elatior *Begonia* and hereinafter referred to by the name 'KRHARPI01'.

The new *Begonia* plant is a product of a planned breeding program conducted by the Inventor in Ermelo, The Netherlands. The objective of the breeding program is to create new vigorous *Begonia* plants with excellent postproduction longevity and attractive flower color.

The new *Begonia* plant originated from a cross-pollination made by the Inventor in Ermelo, The Netherlands in January, 2010 of a proprietary selection of *Begonia×tuberhybrida* hybrid identified as code number KV01K0172-001, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in September, 2011. Asexual reproduction of the new *Begonia* plant by leaf cuttings taken in a controlled greenhouse environment in Ermelo, The Netherlands since January, 2012 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRHARPI01'. These characteristics in combination distinguish 'KRHARPI01' as a new and distinct *Begonia* plant:

1. Upright to somewhat outwardly spreading and mounded plant habit.
2. Moderately vigorous growth habit.
3. Freely flowering habit.
4. Double flowers that are pinkish red in color and held above the foliar plane.
5. Excellent postproduction longevity.

Plants of the new *Begonia* differ primarily from plants of the female parent selection in flower color as plants of the female parent selection have salmon orange-colored flowers.

Plants of the new *Begonia* differ primarily from plants of the male parent selection in flower color as plants of the male parent selection have light red purple-colored flowers.

Plants of the new *Begonia* can be compared to plants of *Begonia×hiemalis* 'Dark Netja', not patented. In side-by-side comparisons conducted in Ermelo, The Netherlands, plants of the new *Begonia* differ primarily from plants of 'Dark Netja' in flower color as plants of 'Dark Netja' have light pink-colored flowers. In addition, plants of the new *Begonia* have double flowers whereas plants of 'Dark Netja' have semi-double flowers.

Plants of the new *Begonia* can also be compared to plants of *Begonia×hiemalis* 'Elektra Pink', disclosed in U.S. Plant Pat. No. 18,967. In side-by-side comparisons conducted in Ermelo, The Netherlands, plants of the new *Begonia* differ primarily from plants of 'Elektra Pink' in flower color as plants of 'Elektra Pink' have lighter-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRHARPI01' grown in a container.

The photograph on the second sheet are close up views of the upper (right) and lower (left) surfaces of typical leaves and flowers of 'KRHARPI01' and in the center of the photograph is a close-up view of typical flower buds and pedicel.

DETAILED BOTANICAL DESCRIPTION

The aforementioned photographs and following observations and measurements describe plants grown during the spring in 12-cm containers in a shaded glass-covered greenhouse in Ermelo, The Netherlands and under cultural practices typical of commercial *Begonia* production. During the production of the plants, day temperatures averaged 20° C. and night temperatures averaged 18° C. Plants were eleven weeks old when the photographs and description were taken. In the following description, color references are made to The Royal Horticultural Society Colour Chart, 2015 Edition, except where general terms of ordinary dictionary significance are used.

Botanical classification: *Begonia×hiemalis* 'KRHARPI01'.

Parentage:

- *Female, or seed, parent*.—Proprietary selection of *Begonia×tuberhybrida* hybrid identified as code number KV01K0172-001, not patented.
- *Male, or pollen, parent*.—Proprietary selection of *Begonia socotrana* identified as code number S00, not patented.

Propagation:

- *Type*.—By terminal vegetative cuttings.
- *Time to initiate roots, summer and winter*.—About 20 days at temperatures about 20° C.
- *Time to produce a rooted young plant, summer and winter*.—About five weeks at temperatures about 20° C.
- *Root description*.—Fine, fibrous; typically white to orange brown in color, actual color of the roots is dependent on substrate composition, water quality, fertilizer type and formulation, substrate temperature and physiological age of roots.
- *Rooting habit*.—Freely branching; medium density; plants of the new *Begonia* have not been observed to form tubers.

Plant description:

- *Plant habit and form*.—Upright to somewhat outwardly spreading and mounded plant habit; overall plant shape, globular.
- *Growth habit*.—Moderately vigorous growth habit and moderate growth rate; suitable for 12-cm and larger containers; under optimal environmental and cultural conditions, usually about ten weeks are required to produce proportional plants in 12-cm containers.
- *Branching habit*.—Moderately freely branching with about four primary branches each with about two secondary branches.
- *Plant height, soil level to top of foliar plane*.—About 23.5 cm.
- *Plant height, soil level to top of floral plane*.—About 29.5 cm.
- *Plant width*.—About 34.7 cm.
- *Lateral branches*.—Length: About 15 cm. Diameter: About 8 mm. Internode length: About 3.3 cm. Strength: Moderately strong. Aspect: About 20° from vertical. Texture and luster: Smooth, glabrous; moderately glossy. Color, developing: Close to 144B. Color, developed: Close to between 144B and 146C.
- *Leaves*.—Arrangement: Alternate, simple. Length: About 16.2 cm. Width: About 11.3 cm. Shape: Ovate. Apex: Acute. Base: Oblique, lobes free. Margin: Coarsely bi-crenate to serrate; strongly undulate. Texture and luster, upper surface: Smooth, glabrous; slightly velvety; moderately glossy. Texture and luster, lower surface: Sparsely pubescent along venation; moderately glossy. Venation pattern: Laciniate. Color: Developing leaves, upper surface: Close to 143A. Developing leaves, lower surface: Close to 147C. Fully expanded leaves, upper surface: Darker than between 139A and 147A; venation, close to 143A. Fully expanded leaves, lower surface: Close to 147C, strongly tinged with close to 176A; venation, close to 146A. Petioles: Length: About 7.1 cm. Diameter: About 5.5 mm. Strength: Low, flexible. Texture and luster, upper and lower surfaces: Sparsely pubescent; moderately glossy. Color, upper surface: Close to 144B; distally, close to between 176B and 177A. Color, lower surface: Close to 144B to 144C; distally, slightly tinged with close to 176B. Stipules: Length: About 1.2 cm. Width: About 9 mm. Shape: Broadly ovate. Apex: Obtuse. Base: Broadly cuneate. Margin: Entire. Texture and luster, upper and lower surfaces: Smooth, glabrous; moderately glossy. Color, upper and lower surfaces: Close to 179D; venation, close to 180C to 180D.

Flower description:

- *Flower appearance and flowering habit*.—Fully double rotate flowers with four tepals and numerous tepaloids; flowers arranged in axillary compound cymes; freely flowering habit with typically about seven flowers per cyme and about 170 flowers and flower buds developing per plant; many cymes in flower simultaneously; flowers positioned above the foliar plane and face upright to outwardly.
- *Natural flowering season*.—Plants begin flowering about six weeks after planting; plants will flower year round regardless of nyctoperiod, however plants flower earlier and more abundantly from spring into the autumn in The Netherlands.
- *Postproduction longevity*.—Individual flowers last about ten days on the plant; flowers not persistent; excellent postproduction longevity, plants maintain good substance for about five weeks in an interior environment.
- *Fragrance*.—None detected.
- *Inflorescence height*.—About 15.9 cm.
- *Inflorescence diameter*.—About 11.3 cm.
- *Flowers*.—Shape: Rotate, fully double. Diameter: About 6.8 cm. Depth (height): About 3 cm.
- *Flower buds*.—Length: About 1.8 cm. Diameter: About 0.5 cm to 2.1 cm. Shape: Broadly ovate to nearly circular, flattened. Texture and luster: Glabrous; velvety; slightly glossy. Color: Close to 50C.
- *Tepals*.—Quantity and arrangement per flower: Usually about four per flower arranged in two whorls.

Length, lower tepals: About 3.5 cm. Width, lower tepals: About 4.2 cm. Length, upper tepals: About 2.9 cm. Width, upper tepals: About 2.9 cm. Shape, lower tepals: Reniform. Shape, upper tepals: Broadly ovate to broadly obovate. Apex, all tepals: Rounded. Base, all tepals: Rounded. Margin, lower tepals: Entire; slightly undulate. Margin, upper tepals: Entire; moderately undulate. Texture and luster, upper surface, lower tepals: Smooth, glabrous; moderately velvety; matte. Texture and luster, lower surface, lower tepals: Smooth, glabrous; moderately velvety; slightly glossy. Texture and luster, upper and lower surfaces, upper tepals: Smooth, glabrous; moderately velvety; matte. Color, all tepals: When opening, upper surface: Close to 50B. When opening, lower surface: Close to 50C; towards the margins, close to 50B. Fully opened, upper surface: Close to between 47C and 50B; venation, similar to lamina color; color does not change with development. Fully opened, lower surface: Close to 52C; towards the margins, close to 52B; venation, similar to lamina color; color does not change with development.

*Tepaloids*.—Quantity and arrangement per flower: Usually about 25 per flower arranged in about five whorls. Length: About 1.2 cm to 2.1 cm. Width: About 0.7 cm to 2.1 cm. Shape: Broadly obovate. Apex: Rounded to shallowly cleft. Base: Broadly attenuate. Margin: Entire. Texture and luster, upper and lower surfaces: Smooth, glabrous; moderately velvety; matte. Color: When opening, upper and lower surfaces: Close to 50C; towards the base, close to 1B. Fully opened, upper surface: Close to between 50B and 52B to 52C; venation, similar to lamina color; color does not change with development. Fully opened, lower surface: Close to 50C; venation, similar to lamina color; color does not change with development.

*Peduncles*.—Length: About 7.9 cm. Diameter: About 4.5 mm to 5 mm. Strength: Moderately strong. Aspect: About 20° from lateral branch axis. Texture and luster: Smooth, glabrous; moderately glossy. Color: Close to 144B.

*Pedicels*.—Length: About 2.4 cm. Diameter: About 2 mm. Strength: Moderately strong. Aspect: About 35° from peduncle axis. Texture and luster: Smooth, glabrous; moderately glossy. Color: Close to 145A tinged with close to 153D.

*Flower bracts*.—Quantity per flower: Two. Length: About 1.9 cm. Width: About 1.6 cm. Shape: Ovate. Margin: Entire. Texture and luster, upper and lower surfaces: Smooth, glabrous; slightly glossy. Color, upper surface: Close to 146C to 146D tinged with close to 180B to 180C; venation, close to 152B to 152C. Color, lower surface: Close to 146C to 146D; venation, close to 152B to 152C.

*Reproductive organs*.—Stamens: None observed. Pistils: None observed.

*Seeds and fruits*.—Seed and fruit production have not been observed as reproductive organs are not formed.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRHARPI01' as illustrated and described.

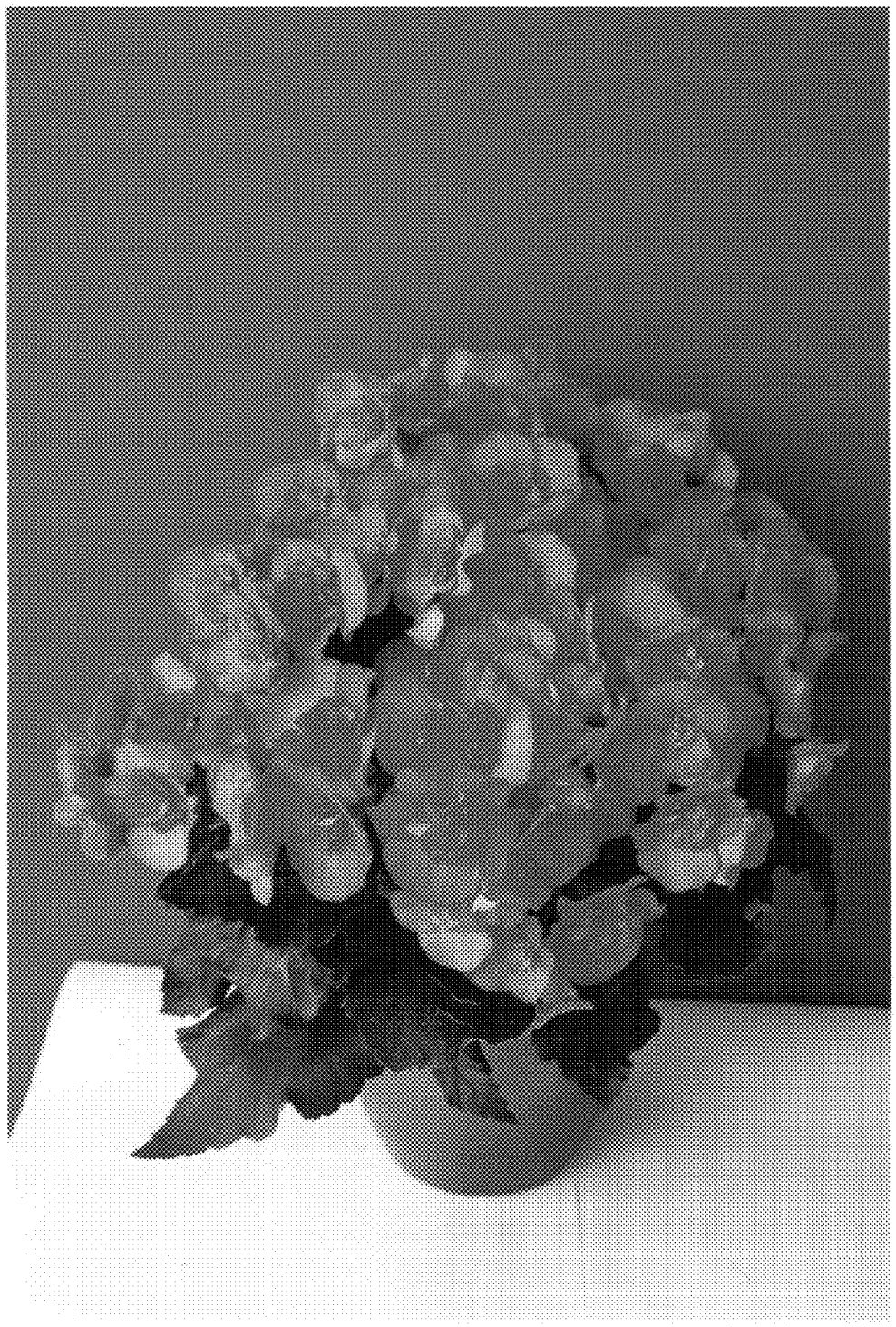

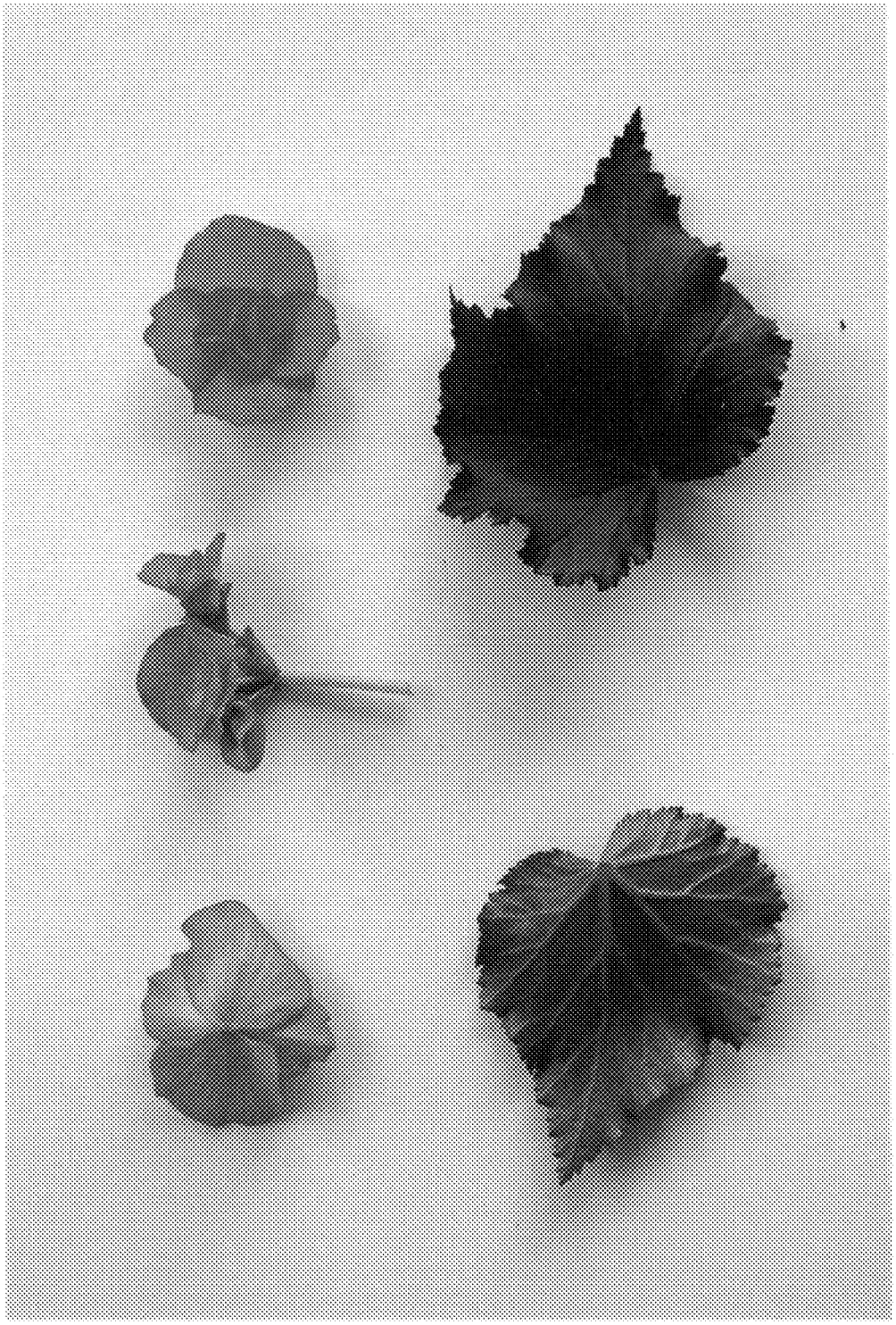

* * * * *